(12) United States Patent
DeJule

(10) Patent No.: US 8,408,211 B2
(45) Date of Patent: Apr. 2, 2013

(54) METHOD OF FACILITATING INHALATION OF CONTROLLED QUANTITIES OF EXHALED AIR

(76) Inventor: Ruthanna DeJule, Chicago, IL (US)

(*) Notice: Subject to any disclaimer, the term of this patent is extended or adjusted under 35 U.S.C. 154(b) by 649 days.

(21) Appl. No.: 12/653,314

(22) Filed: Dec. 11, 2009

(65) Prior Publication Data

US 2011/0139160 A1 Jun. 16, 2011

(51) Int. Cl.
*A61M 15/08* (2006.01)
*A62B 18/02* (2006.01)
*A62B 7/00* (2006.01)

(52) U.S. Cl. ......... 128/207.18; 128/207.13; 128/206.27; 128/206.21; 128/203.22; 128/200.24

(58) Field of Classification Search ............ 128/200.24, 128/204.12, 206.11, 206.18; 606/204.45, 606/157; 482/13
See application file for complete search history.

(56) References Cited

U.S. PATENT DOCUMENTS

| | | | | |
|---|---|---|---|---|
| 2,007,330 A * | 7/1935 | Hicks | 128/203.28 |
| 2,015,617 A * | 9/1935 | Claudius | 606/157 |
| 2,693,799 A * | 11/1954 | Herman, Jr. | 128/201.18 |
| 2,777,442 A * | 1/1957 | Zelano | 128/206.11 |
| 3,451,392 A * | 6/1969 | Cook et al. | 128/206.11 |
| 3,513,843 A * | 5/1970 | Exler | 128/203.25 |
| 3,949,984 A * | 4/1976 | Navara | 482/13 |
| 4,192,301 A * | 3/1980 | Hardwick | 128/205.17 |
| 4,275,722 A * | 6/1981 | Sorensen | 128/200.24 |
| 4,508,116 A * | 4/1985 | Duncan et al. | 128/203.28 |
| 4,628,926 A * | 12/1986 | Duncan et al. | 128/203.28 |
| 5,154,167 A * | 10/1992 | Hepburn | 128/200.24 |
| 5,899,832 A * | 5/1999 | Hougen | 482/13 |
| 5,910,071 A * | 6/1999 | Hougen | 482/13 |
| 5,931,852 A * | 8/1999 | Brennan | 606/199 |
| 6,083,141 A * | 7/2000 | Hougen | 482/13 |
| 6,880,557 B2 * | 4/2005 | Downey | 128/205.28 |
| 7,055,523 B1 * | 6/2006 | Brown | 128/206.11 |
| 7,108,198 B2 * | 9/2006 | Altadonna, Jr. | 239/34 |
| 2010/0331877 A1 * | 12/2010 | Li et al. | 606/204.45 |

* cited by examiner

*Primary Examiner* — Annette Dixon
(74) *Attorney, Agent, or Firm* — Wood, Phillips, Katz, Clark & Mortimer

(57) ABSTRACT

A method of intercepting controlled quantities of air exhaled from at least one of two nostrils on an individual's nose to permit inhalation of the intercepted air, including the steps of: providing an air flow intercepting apparatus; and placing the air flow intercepting apparatus in an operative position relative to the individual's nostrils so that as the individual inhales and exhales during repeating breathing cycles: a) a first quantity of exhaled air flows past the air flow intercepting apparatus; and b) a second quantity of exhaled air impinges upon the air flow intercepting apparatus so as to at least one of: i) stagnate; and ii) be redirected by the air flow intercepting apparatus so that at least a portion of the second quantity of exhaled air is drawn into the individual's nostrils as the individual inhales.

21 Claims, 2 Drawing Sheets

METHOD OF FACILITATING INHALATION OF CONTROLLED QUANTITIES OF EXHALED AIR

BACKGROUND OF THE INVENTION

1. Field of the Invention

This invention relates to therapeutic nasal inhalation and, more particularly, to a method for intercepting air exhaled during a normal breathing cycle so that controlled quantities of the exhaled air can be inhaled by an individual.

2. Background Art

It is well known that conditions such as anxiety, chronic stress, asthma, and the like, may lead to over-breathing or hyperventilation. Contrary to intuition, hyperventilation, which can occur with unusually deep or rapid breathing, can create an oxygen deficiency in the blood. The mechanism is as follows. As inhaled oxygen levels exceed the body's metabolic demands, blood $CO_2$ levels decrease and blood carbonic acid levels lower, creating a corresponding increase in blood pH levels making the blood more alkaline. In alkaline blood, oxygen is tightly bound to the hemoglobin impeding the oxygenation of the body's tissues, leading to symptoms such as dizziness and feelings of detachment or numbness and tingling in the toes or fingers, depending on whether the lowered oxygen levels are in the brain or at the extremities.

It is generally accepted that increasing blood $CO_2$ levels is a factor in causing the widening of blood vessels (vasodilation), which leads to a lowering of blood pressure. Many consider that work/life-related stress can trigger a temporary increase in blood pressure. As described by Herbert Benson in "The Relaxation Response," a means of lowering blood pressure can be associated with the body being in a relaxed state.

One way of increasing $CO_2$ levels is by re-breathing $CO_2$ rich exhaled air collected in a paper bag, commonly known to reverse the effects of hyperventilation such as occurs during an anxiety attack.

In the early 1960's, a breathing method was developed that similarly abates hyperventilation by effectively decreasing the amount of oxygen inhaled. Known as the Buteyko breathing technique (BBT), it is based on a theory that "hidden hyperventilation" is a characteristic of asthmatic breathing. While most people have experienced hyperventilation to some degree, studies indicate asthmatics may breathe 2.5 times more air per minute than healthy adults. The BBT teaches asthmatics to breathe less by reducing the depth and frequency of inhalations, thus reducing the amount of inhaled oxygen. The result is that the drop in $CO_2$ levels is reversed and the symptoms of blood alkalinity, dizziness, detachment, etc., that typically occur when one is having difficulty breathing, are reduced.

The BBT has been shown to successfully and safely reduce asthma/hyperventilation symptoms and the need for medication. Though this method was developed nearly 50 years ago, its effectiveness was formally recognized when the British Guideline on the Management of Asthma in 2008 deemed the BBT appropriate for health professionals in the United Kingdom to recommend to their patients. However, to achieve the results reported requires daily exercises over a period of weeks or months.

Apparatus for re-breathing $CO_2$, as described by Exler (U.S. Pat. No. 3,513,843), and for administering $CO_2$, as described by Hicks (U.S. Pat. No. 2,007,330), both use a vessel to collect exhaled air and a mask covering the nose and mouth for re-breathing.

Similarly, the breathing exercise in Navara (U.S. Pat. No. 3,949,984) and the re-breathing apparatus for use with hyperventilating patients, described by Hardwick (U.S. Pat. No. 4,192,301), require an inflatable bag to collect exhaled air, which is re-breathed through a mouth and nose/mouth mask, respectively. Furthermore, Hardwick connects the nose/mouth mask to a proportioning valve to adjust the proportion of re-breathed to fresh air inhaled.

Sorensen (U.S. Pat. No. 4,275,722) teaches a method of mixing exhaled air with fresh air to increase the $CO_2$ content of the air inhaled. However, this is done by using inhalation and exhalation chambers while breathing through the mouth. Other breathing apparatus, Downey (U.S. Pat. No. 6,880,557), Hougen (U.S. Pat. Nos. 5,899,832; 5,910,071; and 6,083,141), and Duncan et al. (U.S. Pat. Nos. 4,508,116; and 4,628,926) have some form of vessel into which exhaled air is collected.

Hepburn (U.S. Pat. No. 5,154,167) describes a lung and chest exercise and developer "that arranges for some of the air expired from the lungs on an outbreath to be collected and then to be breathed back into the lungs on the next inbreath, together with some fresh air." This device has a mouthpiece with a collector bag consisting of a top and bottom portion and a structure for restricting the amount of fresh air. A nosepiece can be added to restrict airflow through the nose. This apparatus requires a collection bag and the mixing of exhaled air with fresh air by restricting airflow in some manner.

SUMMARY OF THE INVENTION

In one form, the invention is directed to a method of intercepting controlled quantities of air exhaled from at least one of two nostrils on an individual's nose to permit inhalation of the intercepted air. The method includes the steps of: providing an air flow intercepting apparatus; and placing the air flow intercepting apparatus in an operative position relative to the individual's nostrils so that as the individual inhales and exhales during repeating breathing cycles: a) a first quantity of air exhaled from at least one of the individual's nostrils flows past the air flow intercepting apparatus; and b) a second quantity of air exhaled from the at least one of the individual's nostrils impinges upon the air flow intercepting apparatus so as to at least one of: i) stagnate; and ii) be redirected by the air flow intercepting apparatus so that at least a portion of the second quantity of exhaled air is drawn into the individual's nostrils as the individual inhales.

In one form, the step of placing the air flow intercepting apparatus in an operative position involves releasably attaching the air flow intercepting apparatus to the individual's nose.

In one form, the step of releasably attaching the air flow intercepting apparatus to the individual's nose involves situating the air flow intercepting apparatus so that a part of the individual's nose is releasably captively held between spaced portions of the air flow intercepting apparatus.

In one form, the individual's nose has a septum and the step of releasably attaching the air flow intercepting apparatus to the individual's nose involves directing the spaced portions one each into the individual's nostrils so that the individual's septum is releasably captively held between the spaced portions.

In one form, the step of providing an air flow intercepting apparatus involves providing an air flow intercepting apparatus with a body defining a first surface that is spaced below one of the individual's nostrils and one of: a) concavely curved opening towards the one of the individuals nostrils; and b) generally flat, with the air flow intercepting apparatus in the operative position.

In one form, the step of providing an air flow intercepting apparatus involves providing an air flow intercepting apparatus wherein the body defines a second surface that is spaced below the other of the individual's nostrils and one of: a) concavely curved opening towards the other of the individual's nostrils; and b) generally flat, with the air flow intercepting apparatus in the operative position.

In one form, the step of releasably attaching the air flow intercepting apparatus to the individual's nose involves situating the air flow intercepting apparatus so that a part of the individual's nose is releasably captively held between spaced portions of the air flow intercepting apparatus.

In one form, the step of providing an air flow intercepting apparatus involves providing an air flow intercepting apparatus wherein the body has an overall shape of a "T" with a stem and crossbar and the crossbar of the T is defined by the spaced portions of the air flow intercepting apparatus.

In one form, the step of providing an air flow intercepting apparatus involves providing an air flow intercepting apparatus wherein one of the spaced portions of the air flow intercepting apparatus has a first discrete projection that bears against a part of the individual's nose with the air flow intercepting apparatus in the operative position.

In one form, the individual's nose has a septum and the step of providing an air flow intercepting apparatus involves providing an air flow intercepting apparatus wherein the first discrete projection bears against the individual's septum with the air flow intercepting apparatus in the operative position.

In one form, the step of providing an air flow intercepting apparatus involves providing an air flow intercepting apparatus wherein the other of the spaced portions of the air flow intercepting apparatus has a second discrete projection that bears against a part of the individual's nose with the air flow intercepting apparatus in the operative position.

In one form, the step of providing an air flow intercepting apparatus involves providing an air flow intercepting apparatus wherein the first and second discrete projection project towards each other, one each from the spaced portions.

In one form, the step of providing an air flow intercepting apparatus involves providing an air flow intercepting apparatus wherein the body has a main portion from which the spaced portions project in cantilever fashion.

In one form, the step of providing an air flow intercepting apparatus involves providing an air flow intercepting apparatus wherein the spaced portions have free ends and the projections are located one each on the spaced portions adjacent to the free end of the respective spaced portions.

In one form, the user's nose has a septum and the step of providing an air flow intercepting apparatus involves providing an air flow intercepting apparatus wherein the spaced portions are flexible towards and away from each other and resiliently captively engage the individual's septum to thereby resiliently maintain the air flow intercepting apparatus in the operative position.

In one form, the step of providing an air flow intercepting apparatus involves providing an air flow intercepting apparatus wherein the first and second body surfaces are each cup shaped.

In one form, the individual's nose has a width and the step of providing an air flow intercepting apparatus involves providing an air flow intercepting apparatus wherein the first and second body surfaces are elongate along the width of the individual's nose with the air flow intercepting apparatus in the operative position.

In one form, the step of providing an air flow intercepting apparatus involves providing an air flow intercepting apparatus wherein the main body portion and spaced projections are formed as one piece.

In one form, the individual's nose has a width and the step of providing an air flow intercepting apparatus involves providing an air flow intercepting apparatus wherein the first and second surfaces cooperatively have a width nominally matched to the width of the individual's nose with the air flow intercepting apparatus in the operative position.

In one form, the step of providing an air flow intercepting apparatus involves providing an air flow intercepting apparatus wherein the one piece is made from molded plastic.

DETAILED DESCRIPTION OF THE PREFERRED EMBODIMENT

Figure 1:
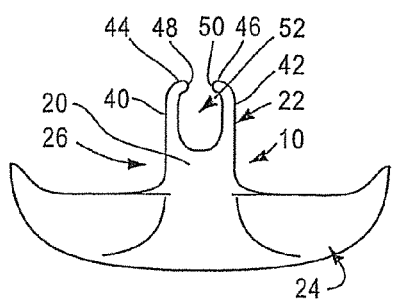
FIG. 1 is a front elevation view of an air flow intercepting apparatus according to the present invention.
Figure 2:
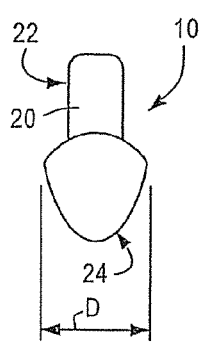
FIG. 2 is a side elevation view of the apparatus in FIG. 1.
Figure 4:
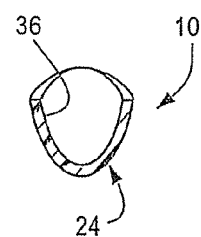
FIG. 4 is a cross-sectional view of the apparatus taken along line 4-4 of FIG. 3.

In FIGS. 1-5, an air flow intercepting apparatus, according to the present invention, is depicted at 10, with the apparatus 10 shown in an operative position relative to the nose 12 of an individual 14 and, more particularly, with respect to that individual's nostrils 16, 18, at the bottom thereof.

The apparatus 10 has a body 20 with an overall shape of a "T", with the stem of the T defining a mounting section 22 and the crossbar of the T defining a flow intercepting section 24. The body 20 has a main portion 26, consisting of a part of the stem of the T and the flow intercepting section 24.

Figure 5:
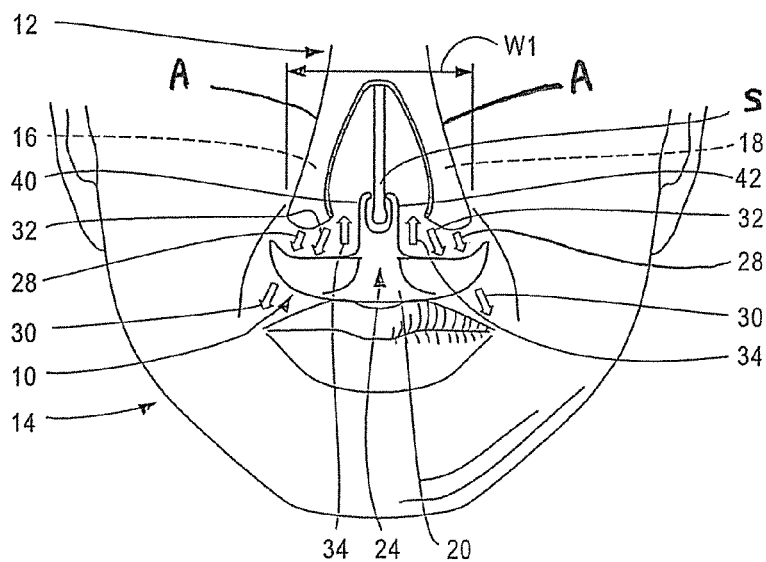
FIG. 5 is a fragmentary, front elevation view of the facial region of an individual with the apparatus of FIGS. 1-4 in an operative position.

The apparatus 10 is designed so that upon being placed in the operative position of FIG. 5, a first quantity of air exhaled from the nostrils 16, 18, moving as indicated by the arrows 28, flows past the flow intercepting section 24, as indicated by the arrows 30. A second quantity of air exhaled from the nostrils 16, 18 impinges upon the apparatus at the flow intercepting section 24, moving as indicated by the arrows 32, so as to at least one of: a) stagnate; and b) be redirected so that at least a portion of the second quantity of exhaled air is drawn into the individuals nostrils 16, 18, moving as indicated by the arrows 34, as the individual subsequently inhales. As the individual inhales and exhales repeatedly during normal breathing cycles, a quantity of exhaled air is intercepted by the apparatus 10 so that at least a controlled portion thereof is capable of being inhaled.

The body 20 has first and second surfaces 36, 38 that are situated, one each, respectively below the nostrils 16, 18 in subjacent, spaced relationship, as shown in FIG. 5, with the apparatus 10 in the operative position. The surfaces 36, 38 are spaced a first distance below the nostrils 16, 18 so that the second quantity of air exhaled from the nostrils 16, 18 departs the nostrils 16, 18 and travels the first distance before impinging upon the surfaces 36, 38. The precise shape of the surfaces 36, 38 is not critical to the present invention as the shape thereof could be altered depending upon the desired deflection pattern and the volume quantity of the air that is desired to be made available for re-breathing. In the depicted form, the surfaces 36, 38 have a solid shape that extends over a majority of the width of the nostrils 16, 18 between the individual's nasal septum S and the alar A.

In the one preferred form in FIGS. 1-5, the surfaces 36, 38 are each concavely curved, opening towards their respective nostrils 16, 18. While the surfaces 36, 38 are described as separate in nature, the surfaces 36, 38 could be viewed as contiguous so as to be considered a single surface. For simplicity, whether there are two discrete surfaces 36, 38, or one surface with separate surface portions, the surfaces will be considered to be, and described herein as, separate.

To releasably maintain the apparatus 10 in the operative position of FIG. 5, the mounting section 22 is made with spaced portions/legs 40, 42 that project in cantilever fashion away from the main portion 26 of the body 20. The legs 40, 42 terminate at free ends 44, 46. Discrete projections 48, 50 are provided adjacent to, and more preferably at, the free ends 44, 46, respectively. The projections 48, 50 project towards each other from their respective leg 40, 42.

Figure 6:
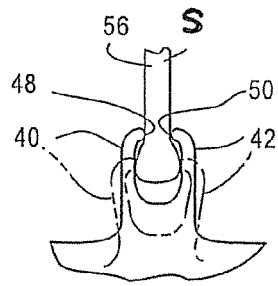
FIG. 6 is an enlarged, fragmentary, front elevation view of a portion of the apparatus that releasably engages the individual's septum with the apparatus in the operative position of FIG. 5.

The legs 40, 42 are spaced from each other to define a region 52 that is configured to accept the individual's nasal septum S with the apparatus 10 in the operation position, as seen also in FIG. 6. The nasal septum S is considered to be a part of the "nose", as described and claimed herein.

To operatively position the apparatus, the apparatus 10 is initially situated so that the free leg ends 44, 46 reside beneath the individual's septum S, with the septum S located generally in a centered relationship therebetween. The apparatus 10 is then directed upwardly. The spacing between the projections 48, 50 on the legs 40, 42 is such that as the free ends 44, 46 of the legs 40, 42 move upwardly to against the septum S, they must be deflected away from each other, as seen in dotted lines in FIG. 6, to allow the septum S to move into the region 52 under a continuing upward moving force. This is made possible by constructing the legs 40, 42 so that they are resiliently flexible outwardly and will tend back towards an undeformed state.

Continued upward movement of the apparatus 10 causes the projections 48, 50 to vertically align with a narrower region 56 of the septum S. Residual forces in the bent legs 40, 42 urge them resiliently back towards each other so as to captively embrace the septum region 56 with a moderate holding force that is adequate to preclude downward shifting of the apparatus 10 from its operative position in FIGS. 5 and 6 under its own weight and any forces applied through the normal exhaled air flow. At the same time, the captive force should not be great enough to cause the individual discomfort with the apparatus 10 in place.

To allow for an economical, lightweight construction, the apparatus 10 may be molded as one piece from a plastic material. The plastic material also affords the flexibility required to permit the deflection of the legs 40, 42 and production of the necessary resilient holding force by the legs with the apparatus 10 in the operative position therefor.

The apparatus may be made, in whole or in part, from either a relatively rigid, shape retentive construction, or one that is, in whole or in part, flexible. If flexibility is desired, it is possible to make the apparatus 10 of a material that may flex upon being impinged upon by the flow of exhaled air. This may be desirable for purposes of weight and cost reduction, and may also be exploited to strategically control air interception reaction.

The material construction may be bendable into different maintainable shapes that are selected for desired air flow control properties.

It is desirable that the apparatus 10 have a profile that does not become obtrusive or discommode the individual 14 as he/she navigates through a normal routine or sleeps in sitting or prone positions. In the depicted embodiment, the body 20 and surfaces 36, 38 are made with a width W that is nominally matched to the width W1 of the individual's nose 12. The width W might be slightly less than or greater than the width W1, again depending upon the desired air flow interception properties.

Figure 3:
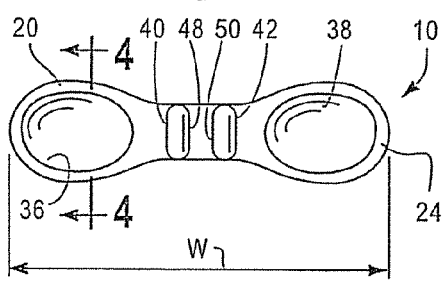
FIG. 3 is a plan view of the apparatus in FIGS. 1 and 2.

As seen in FIG. 3, the flow intercepting section 24 has a configuration wherein the surfaces 36, 38 are elongate in a widthwise direction. The perimeter has an overall figure "8" shape to nominally conform to the individual's sub-nasal facial region. The "8" shape also softens corners/edges so as not to create user discomfort upon contact therewith. This shape is but one of many different shapes contemplated. As but one example, the mid-width fore-and-aft narrowing can be eliminated in this embodiment and that shown in FIGS. 8-10, described below, as shown in dotted lines in exemplary FIG. 9.

The depth D of the apparatus 10 can be selected so that the apparatus 10 performs consistently with the above objectives.

Many variations from the basic configuration shown for the apparatus in FIGS. 1-6 are contemplated. The apparatus 10 is shown in but one exemplary form in these Figures.

As just one example, the apparatus might be configured to intercept air primarily from only one of the nostrils 16, 18.

Figure 7:
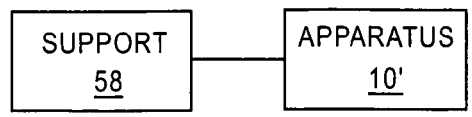
FIG. 7 is a schematic representation of a modified form of apparatus, according to the invention.

While the apparatus 10 is conveniently and simply press fit into its operative position and releasably held upon the septum S of the individual 14, it is contemplated that the same basic type of apparatus 10', as shown generically/schematically in FIG. 7, might be maintained in its operative position by a support 58, that may be a part of the individual 14, other than at the septum S, or an independent support. As examples, the apparatus 10' might be held in place by being clipped to the outside of the nose 12, taped to the nose 12, held by the ears, or supported other than at the head region. The schematic showing in FIG. 7 is intended to encompass all such, and other, variations.

Figure 8:
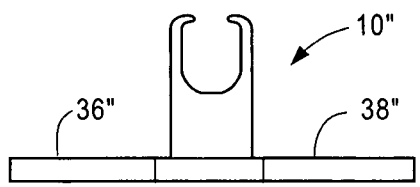
FIG. 8 is a front elevation view of a further modified form of apparatus, according to the present invention.
Figure 9:
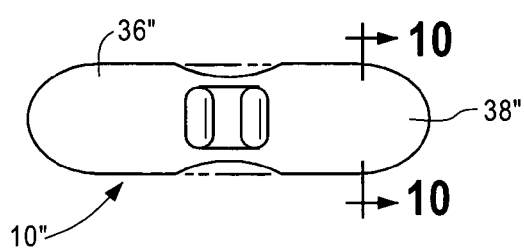
FIG. 9 is a plan view of the apparatus in FIG. 8.
Figure 10:
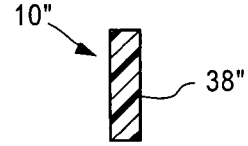
FIG. 10 is a cross-sectional view of the apparatus taken along line 10-10 of FIG. 9.

Another exemplary variation is shown for the inventive apparatus 10" in FIGS. 8-10. The apparatus 10" has substantially the same arrangement of components as, and functions similarly to, the apparatus 10, with the exception that the surfaces 36", 38", corresponding to the surfaces 36, 38, are substantially flat, as opposed to being cup-shaped.

Figure 11:
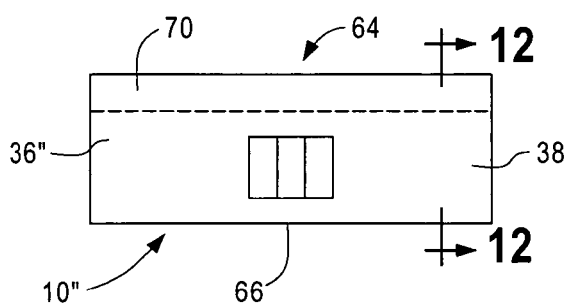
FIG. 11 is a plan view of a still further modified form of apparatus, according to the invention.
Figure 12:
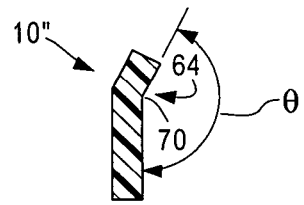
FIG. 12 is a cross-sectional view of the apparatus taken along line 12-12 of FIG. 11.

As a further alternative, as shown in FIGS. 11 and 12, an apparatus 10" may be provided with surfaces 36", 38" that terminate at an offset 64 that is remote from the edge 66 that resides adjacent to a user's face. This shape deflects a greater quantity of exhaled air back towards a user's nostrils 16, 18 than would a corresponding shape, absent the offset 64. The offset has a surface 70 that makes an angle θ with the surfaces 36", 38", and captures and deflects towards the nostrils 16, 18 exhaled air that might otherwise flow past the apparatus 10". This same effect can be achieved by other shapes, such as curved, that would intercept and redirect exhaled air in a like manner.

Figure 13:
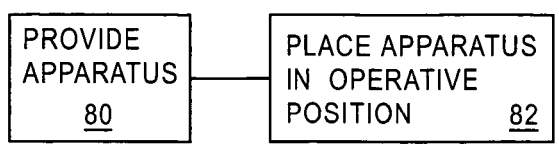
FIG. 13 is a flow diagram representation of a method of intercepting controlled quantities of exhaled air to permit inhalation of at least a portion of the intercepted air according to the invention.

With the structures as described above, a method, as shown in block diagram form in FIG. 13, may be carried out to intercept controlled quantities of air exhaled from at least one of two nostrils on an individual's nose to permit inhalation of the intercepted air.

As shown at block 80, an air flow intercepting apparatus is provided.

As shown at block 82, the air flow intercepting apparatus is placed in the operative position relative to the individual's nostrils so that as the individual inhales and exhales during repeated breathing cycles: a) a first quantity of air exhaled from at least one of the individual's nostrils flows past the air flow intercepting apparatus; and b) a second quantity of air exhaled from the at least one of the individual's nostrils impinges upon an air flow intercepting apparatus so as to at least one of: i) stagnate; and ii) be redirected so that at least a portion of the second quantity of exhaled air is drawn into the individual's nostrils as the individual inhales.

The foregoing disclosure of specific embodiments is intended to be illustrative of the broad concepts comprehended by the invention.

The invention claimed is:

1. A method of intercepting controlled quantities of air exhaled from at least one of two nostrils on an individual's nose to permit inhalation of the intercepted air, the two nostrils each having a width between a septum and an alar on the individual's nose, the method comprising the steps of:
   providing an air flow intercepting apparatus; and
   placing the air flow intercepting apparatus in an operative position relative to the individual's nostrils so that as the individual inhales and exhales during repeating breathing cycles: a) a first quantity of air exhaled from at least one of the individual's nostrils flows past the air flow intercepting apparatus; and b) a second quantity of air exhaled from the at least one of the individual's nostrils impinges upon the air flow intercepting apparatus so as to at least one of: i) stagnate; and ii) be redirected by the air flow intercepting apparatus so that at least a portion of the second quantity of exhaled air is drawn into the individual's nostrils as the individual inhales,
   wherein the step of providing an air flow intercepting apparatus comprises providing an air flow intercepting apparatus with a body defining a first surface that is spaced a first distance below the one of the individual's nostrils so that the second quantity of air exhaled from the one nostril travels the first distance before impinging upon the first surface,
   wherein the first surface comprises a solid surface extending over a majority of the width of the one nostril.

2. The method of intercepting controlled quantities of air exhaled from at least one of two nostrils on an individual's nose according to claim 1 wherein the step of placing the air flow intercepting apparatus in an operative position comprises releasably attaching the air flow intercepting apparatus to the individual's nose.

3. The method of intercepting controlled quantities of air exhaled from at least one of two nostrils on an individual's nose according to claim 2 wherein the step of releasably attaching the air flow intercepting apparatus to the individual's nose comprises situating the air flow intercepting apparatus so that a part of the individual's nose is releasably captively held between spaced portions of the air flow intercepting apparatus.

4. The method of intercepting controlled quantities of air exhaled from at least one of two nostrils on an individual's nose according to claim 3 wherein the step of releasably attaching the air flow intercepting apparatus to the individual's nose comprises directing the spaced portions one each into the individual's nostrils so that the individual's septum is releasably captively held between the spaced portions.

5. The method of intercepting controlled quantities of air exhaled from at least one of two nostrils on an individual's nose according to claim 1 wherein the step of providing an air flow intercepting apparatus comprises providing an air flow intercepting apparatus wherein the first surface is concavely curved opening towards the one of the individuals' nostrils with the air flow intercepting apparatus in the operative position.

6. The method of intercepting controlled quantities of air exhaled from at least one of two nostrils on an individual's nose according to claim 5 wherein the step of providing an air flow intercepting apparatus comprises providing an air flow intercepting apparatus wherein the body defines a second surface that is spaced a distance below the other of the individual's nostrils and one of: a) concavely curved opening towards the other of the individual's nostrils; and b) generally flat with the air flow intercepting apparatus in the operative position.

7. The method of intercepting controlled quantities of air exhaled from at least one of two nostrils on an individual's nose according to claim 6 wherein the step of releasably attaching the air flow intercepting apparatus to the individual's nose comprises situating the air flow intercepting apparatus so that a part of the individual's nose is releasably captively held between spaced portions of the air flow intercepting apparatus.

8. The method of intercepting controlled quantities of air exhaled from at least one of two nostrils on an individual's nose according to claim 7 wherein the step of providing an air flow intercepting apparatus comprises providing an air flow intercepting apparatus wherein the body has an overall shape of a "T" with a stem and crossbar and the crossbar of the T is defined by the spaced portions of the air flow intercepting apparatus.

9. The method of intercepting controlled quantities of air exhaled from at least one of two nostrils on an individual's nose according to claim 8 wherein the step of providing an air flow intercepting apparatus comprises providing an air flow intercepting apparatus wherein one of the spaced portions of the air flow intercepting apparatus has a first discrete projection that bears against a part of the individual's nose with the air flow intercepting apparatus in the operative position.

10. The method of intercepting controlled quantities of air exhaled from at least one of two nostrils on an individual's nose according to claim 9 wherein the step of providing an air flow intercepting apparatus comprises providing an air flow intercepting apparatus wherein the first discrete projection bears against the individual's septum with the air flow intercepting apparatus in the operative position.

11. The method of intercepting controlled quantities of air exhaled from at least one of two nostrils on an individual's nose according to according to claim 10 wherein the step of providing an air flow intercepting apparatus comprises providing an air flow intercepting apparatus wherein the other of the spaced portions of the air flow intercepting apparatus has a second discrete projection that bears against a part of the individual's nose with the air flow intercepting apparatus in the operative position.

12. The method of intercepting controlled quantities of air exhaled from at least one of two nostrils on an individual's nose according to claim 11 wherein the step of providing an air flow intercepting apparatus comprises providing an air flow intercepting apparatus wherein the first and second discrete projection project towards each other, one each from the spaced portions.

13. The method of intercepting controlled quantities of air exhaled from at least one of two nostrils on an individual's nose according to claim 12 wherein the step of providing an air flow intercepting apparatus comprises providing an air flow intercepting apparatus wherein the body comprises a main portion from which the spaced portions project in cantilever fashion.

14. The method of intercepting controlled quantities of air exhaled from at least one of two nostrils on an individual's nose according to claim 13 wherein the step of providing an air flow intercepting apparatus comprises providing an air flow intercepting apparatus wherein the spaced portions have free ends and the projections are located one each on the spaced portions adjacent to the free end of the respective spaced portions.

15. The method of intercepting controlled quantities of air exhaled from at least one of two nostrils on an individual's nose according to claim 14 wherein the step of providing an air flow intercepting apparatus comprises providing an air flow intercepting apparatus wherein the spaced portions are flexible towards and away from each other and resiliently captively engage the individual's septum to thereby resiliently maintain the air flow intercepting apparatus in the operative position.

16. The method of intercepting controlled quantities of air exhaled from at least one of two nostrils on an individual's nose according to claim 1 wherein the step of providing an air flow intercepting apparatus comprises providing an air flow intercepting apparatus wherein the first surface is generally flat.

17. The method of intercepting controlled quantities of air exhaled from at least one of two nostrils on an individual's nose according to claim 13 wherein the step of providing an air flow intercepting apparatus comprises providing an air flow intercepting apparatus wherein the main body portion and spaced projections are formed as one piece.

18. The method of intercepting controlled quantities of air exhaled from at least one of two nostrils on an individual's nose according to claim 6 wherein the individual's nose has a width and the step of providing an air flow intercepting apparatus comprises providing an air flow intercepting apparatus wherein the first and second surfaces cooperatively have a width nominally matched to the width of the individual's nose with the air flow intercepting apparatus in the operative position.

19. The method of intercepting controlled quantities of air exhaled from at least one of two nostrils on an individual's nose according to claim 6 wherein the step of providing an air flow intercepting apparatus comprises providing an air flow intercepting apparatus wherein the first and second body surfaces are each cup shaped.

20. The method of intercepting controlled quantities of air exhaled from at least one of two nostrils on an individual's nose according to claim 19 wherein the individual's nose has a width and the step of providing an air flow intercepting apparatus comprises providing an air flow intercepting apparatus wherein the first and second body surfaces are elongate along the width of the individual's nose with the air flow intercepting apparatus in the operative position.

21. The method of intercepting controlled quantities of air exhaled from at least one of two nostrils on an individual's nose according to claim 17 wherein the step of providing an air flow intercepting apparatus comprises providing an air flow intercepting apparatus wherein the one piece is made from molded plastic.

* * * * *